(12) United States Patent
Dalton et al.

(10) Patent No.: US 7,855,229 B2
(45) Date of Patent: *Dec. 21, 2010

(54) TREATING WASTING DISORDERS WITH SELECTIVE ANDROGEN RECEPTOR MODULATORS

(75) Inventors: James T. Dalton, Upper Arlington, OH (US); Duane D. Miller, Germantown, TN (US); Mitchell S. Steiner, Germantown, TN (US); Karen A. Veverka, Cordova, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 1312 days.

This patent is subject to a terminal disclaimer.

(21) Appl. No.: 11/220,414

(22) Filed: Sep. 7, 2005

(65) Prior Publication Data

US 2006/0111441 A1 May 25, 2006

Related U.S. Application Data

(63) Continuation-in-part of application No. 11/146,427, filed on Jun. 7, 2005, now Pat. No. 7,622,503, which is a continuation-in-part of application No. 10/961,380, filed on Oct. 12, 2004, and a continuation-in-part of application No. 10/861,923, filed on Jun. 7, 2004, which is a continuation-in-part of application No. 10/310,150, filed on Dec. 5, 2002, now Pat. No. 7,547,728, and a continuation-in-part of application No. 10/863,524, filed on Jun. 9, 2004, now abandoned, which is a continuation-in-part of application No. 10/371,213, filed on Feb. 24, 2003, now Pat. No. 7,026,500, which is a continuation-in-part of application No. 10/270,232, filed on Oct. 15, 2002, now Pat. No. 6,838,484, which is a continuation-in-part of application No. 09/935,045, filed on Aug. 23, 2001, now Pat. No. 6,569,896.

(60) Provisional application No. 60/510,138, filed on Oct. 14, 2003, provisional application No. 60/336,185, filed on Dec. 6, 2001, provisional application No. 60/300,083, filed on Jun. 25, 2001, provisional application No. 60/367,355, filed on Aug. 24, 2000.

(51) Int. Cl.
*A61K 31/275* (2006.01)
*A61K 31/32* (2006.01)
*A61K 31/16* (2006.01)
*A61K 31/165* (2006.01)

(52) U.S. Cl. .............. 514/522; 514/524; 514/493; 514/616; 514/619

(58) Field of Classification Search ............. 514/522, 514/524, 493, 616, 619
See application file for complete search history.

(56) References Cited

U.S. PATENT DOCUMENTS

| 3,239,345 A | 3/1966 | Hodge et al. |
|---|---|---|
| 3,865,801 A | 2/1975 | Chiba et al. |
| 3,875,229 A | 4/1975 | Gold |
| 4,036,979 A | 7/1977 | Asato |
| 4,139,638 A | 2/1979 | Neri et al. |
| 4,191,775 A | 3/1980 | Glen |
| 4,239,776 A | 12/1980 | Glen et al. |
| 4,282,218 A | 8/1981 | Glen et al. |
| 4,386,080 A | 5/1983 | Crossley et al. |
| 4,411,890 A | 10/1983 | Momany et al. |
| 4,465,507 A | 8/1984 | Konno et al. |
| 4,636,505 A | 1/1987 | Tucker |
| 4,880,839 A | 11/1989 | Tucker |
| 4,977,288 A | 12/1990 | Kassis et al. |
| 5,162,504 A | 11/1992 | Horoszewicz |
| 5,179,080 A | 1/1993 | Rothkopf et al. |
| 5,441,868 A | 8/1995 | Lin et al. |
| 5,547,933 A | 8/1996 | Lin et al. |
| 5,609,849 A | 3/1997 | Kung |
| 5,612,359 A | 3/1997 | Murugesan et al. |

(Continued)

FOREIGN PATENT DOCUMENTS

| AU | 2002364949 | 6/2003 |
|---|---|---|
| AU | 2003216174 | 9/2003 |
| CA | 2420279 | 2/2002 |
| CA | 2477737 | 9/2003 |
| CA | 2502209 | 4/2004 |

(Continued)

OTHER PUBLICATIONS

U.S. Appl. No. 09/935,044, filed Aug. 23, 2001, Dalton et al.
U.S. Appl. No. 09/935,045, filed Aug. 23, 2001, Dalton et al.
U.S. Appl. No. 09/644,970, filed Aug. 2, 2000, Dalton et al.
Negro-Vilar, A. (1999) "Selective androgen receptor modulators (SARMs): a novel approach to androgen therapy for the new illennium." J. Clin. Endocrin Metabol. 84: 3459-3462.

(Continued)

*Primary Examiner*—Yong S Chong
(74) *Attorney, Agent, or Firm*—Mark S. Cohen; Pearl Cohen Zedek Latzer, LLP

(57) ABSTRACT

This invention provides: 1) a method of treating a subject suffering from a muscle wasting disorder; 2) a method of preventing a muscle wasting disorder in a subject; 3) a method of treating, preventing, suppressing, inhibiting or reducing muscle loss in a subject suffering from a muscle wasting disorder; 4) a method of treating, preventing, inhibiting, reducing or suppressing muscle wasting in a subject suffering from a muscle wasting disorder; and/or 5) a method of treating, preventing, inhibiting, reducing or suppressing muscle protein catabolism in a subject suffering from a muscle wasting disorder, by administering to the subject a selective androgen receptor modulator (SARM) and/or an analog, derivative, isomer, metabolite, pharmaceutically acceptable salt, pharmaceutical product, hydrate, N-oxide, prodrug, polymorph, impurity or crystal of said SARM compound, or any combination thereof.

12 Claims, No Drawings

U.S. PATENT DOCUMENTS

| | | | |
|---|---|---|---|
| 5,618,698 | A | 4/1997 | Lin et al. |
| 5,621,080 | A | 4/1997 | Lin et al. |
| 5,656,651 | A | 8/1997 | Sovak et al. |
| 6,019,957 | A | 2/2000 | Miller et al. |
| 6,043,265 | A | 3/2000 | Murugesan et al. |
| 6,071,957 | A | 6/2000 | Miller et al. |
| 6,160,011 | A | 12/2000 | Miller et al. |
| 6,482,861 | B2 | 11/2002 | Miller et al. |
| 6,492,554 | B2 | 12/2002 | Dalton et al. |
| 6,548,529 | B1 | 4/2003 | Robl et al. |
| 6,569,896 | B2 | 5/2003 | Dalton et al. |
| 6,777,427 | B2 | 8/2004 | Miyakawa et al. |
| 6,838,484 | B2 | 1/2005 | Steiner et al. |
| 6,899,888 | B2 | 5/2005 | Steiner et al. |
| 6,960,474 | B2 | 11/2005 | Salvati et al. |
| 6,995,284 | B2 | 2/2006 | Dalton et al. |
| 6,998,500 | B2 | 2/2006 | Dalton et al. |
| 7,026,500 | B2 | 4/2006 | Dalton et al. |
| 7,041,844 | B2 | 5/2006 | Miller et al. |
| 7,205,437 | B2 | 4/2007 | Dalton et al. |
| 7,344,700 | B2 | 3/2008 | Dalton et al. |
| 7,518,013 | B2 | 4/2009 | Dalton et al. |
| 7,547,728 | B2 | 6/2009 | Dalton et al. |
| 2001/0012839 | A1 | 8/2001 | Miller et al. |
| 2002/0173445 | A1 | 11/2002 | Salvati et al. |
| 2003/0232792 | A1 | 12/2003 | Dalton et al. |
| 2004/0014975 | A1 | 1/2004 | Dalton et al. |
| 2004/0029913 | A1 | 2/2004 | Dalton et al. |
| 2004/0053897 | A1 | 3/2004 | Steiner et al. |
| 2004/0087557 | A1 | 5/2004 | Steiner et al. |
| 2004/0087810 | A1 | 5/2004 | Dalton et al. |
| 2004/0147489 | A1 | 7/2004 | Dalton et al. |
| 2004/0224979 | A1 | 11/2004 | Dalton et al. |
| 2004/0260092 | A1 | 12/2004 | Miller et al. |
| 2004/0260108 | A1 | 12/2004 | Dalton et al. |
| 2004/0265916 | A1 | 12/2004 | Dalton et al. |
| 2005/0038110 | A1 | 2/2005 | Dalton et al. |
| 2005/0137172 | A1 | 6/2005 | Dalton et al. |
| 2006/0004042 | A1 | 1/2006 | Dalton et al. |
| 2006/0009529 | A1 | 1/2006 | Dalton et al. |
| 2006/0035965 | A1 | 2/2006 | Dalton et al. |
| 2006/0111441 | A1 | 5/2006 | Dalton et al. |
| 2006/0183931 | A1 | 8/2006 | Dalton et al. |
| 2006/0229362 | A1 | 10/2006 | Dalton et al. |
| 2007/0066568 | A1 | 3/2007 | Dalton et al. |
| 2007/0123563 | A1 | 5/2007 | Dalton et al. |
| 2007/0161608 | A1 | 7/2007 | Dalton et al. |
| 2007/0173546 | A1 | 7/2007 | Dalton et al. |
| 2007/0281906 | A1 | 12/2007 | Dalton et al. |
| 2009/0088480 | A1 | 4/2009 | Dalton et al. |

FOREIGN PATENT DOCUMENTS

| | | |
|---|---|---|
| CA | 2502355 | 4/2004 |
| CA | 2538095 | 4/2004 |
| CA | 2529464 | 1/2005 |
| EP | 0 040 932 | 2/1981 |
| EP | 0 100 172 | 2/1984 |
| EP | 00 02 892 | 2/1985 |
| EP | 000 2892 | 2/1985 |
| EP | 0253 503 | 12/1991 |
| EP | 0253503 | 12/1991 |
| EP | 668351 | 8/1995 |
| EP | 1221439 | 7/2002 |
| EP | 1401801 | 11/2006 |
| EP | 1801140 | 6/2007 |
| GB | 1360001 | 3/1970 |
| JP | 52-128329 | 10/1977 |
| JP | 54-63047 | 12/1980 |
| JP | 59-033250 | 2/1984 |
| WO | WO 89/07110 | 8/1989 |
| WO | WO 89/07111 | 8/1989 |
| WO | WO 91/05867 | 5/1991 |
| WO | WO 93/04081 | 3/1993 |
| WO | WO 95/19770 | 7/1995 |
| WO | WO 98 05962 | 2/1998 |
| WO | WO 98/05962 | 2/1998 |
| WO | WO 98/53826 | 12/1998 |
| WO | WO 98/55153 | 12/1998 |
| WO | WO 00/01389 | 1/2000 |
| WO | WO 01/27086 | 4/2001 |
| WO | WO/01/27086 | 4/2001 |
| WO | WO 01/27622 | 4/2001 |
| WO | WO 01 27622 | 4/2001 |
| WO | WO 01 28990 | 4/2001 |
| WO | WO 01/28990 | 4/2001 |
| WO | WO 01 34563 | 5/2001 |
| WO | WO 01/34563 | 5/2001 |
| WO | WO 01/68603 | 9/2001 |
| WO | WO 02/00617 | 1/2002 |
| WO | WO 02 00617 | 1/2002 |
| WO | WO 02/16310 | 2/2002 |
| WO | WO/02/22585 | 3/2002 |
| WO | WO 02/22585 | 3/2002 |
| WO | WO 03/011302 | 2/2003 |
| WO | WO 03/049675 | 6/2003 |
| WO | WO 03/065992 | 8/2003 |
| WO | WO 03/074449 | 9/2003 |
| WO | WO/03/077919 | 9/2003 |
| WO | WO 03/077919 | 9/2003 |
| WO | WO 2004/034978 | 4/2004 |
| WO | WO 2004/035736 | 4/2004 |
| WO | WO 2005/000794 | 1/2005 |
| WO | WO 2005/060647 | 7/2005 |

OTHER PUBLICATIONS

Campfield et al., 1995, "Recombinant mouse OB protein: evidence for a peripheral signal linking adiposity and central neural networks" *Science* 269:546-549.

Considine et al., 1995, "Evidence against either a premature stop codon or the absence of obese gene mRNA in human obesity," J. Clin. Invest. 95:2986-2988.

Grundy, 1990, *Disease-a-Month* 36:645-696.

Halaas et al., 1995, "Weight-reducing effects of the plasma protein encoded by the obese gene." *Science* 269:543-546.

Hamilton et al., 1995, "Increased obese mRNA expression in omental fat cells from massively obese humans." Nature Med. 1:953.

Lonnquist et al., 1995, Nature Med. 1:950.

Matsumoto, 1994, "Hormonal therapy of male hypogonadism" Endocrinol. Met. Clin. N. Am. 23:857-75.

Pelleymounter et al., 1995, "Effects of the obese gene product on body weight regulation in ob/ob mice." *Science* 269:540-543.

Singh et al., 2003, "Androgens stimulate myogenic differentiation and inhibit adipogenesis in C3H 10T1/2 pluripotent cells through an androgen receptor-mediated pathway." *Endocrinology*, 144(11):5081-8.

Sefton, 1987, "Implantable pumps." CRC Crit. Ref. Biomed. Eng. 14:201.

Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.

Berger et al., "Concepts and limitations in the application of radiolabeled antiandrogens, estrogens, or androgens as isotropic scanning agents for the prostate", Invest. Urol, (1975), 1391, 10-16.

Howard Tucker and Glynne J. Chesterson, J. Med Chem. 1988, 31, pp. 885-887, "Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer".

D. McKillop, et al., "Enantioselective metabolism and pharmacokinetics of Casodex in the male rat", Xenobiotica, 1995, vol. 25, No. 6, 623-634.

Leonid Kirkovsky, et al., "[$^{125}$I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.

David T. Baird and Anna F. Glasier, "Hormonal Contraception—Drug Therapy", The New England Journal of Medicine, May 27, 1993, pp. 1543-1549.

F.C. W. Wu, "Male Contraception: Current Status and Future Prospects", Clinical Endocrinology, (1988), 29, pp. 443-465.

Carl Djerassi and S.P. Leibo, "A new look at male contraception", Nature, vol. 370, pp. 11-12.

World Health Organisation Task Force on Methods for the Regulation of Male Fertility, "Contraceptive efficacy of testosterone-induced azoospermia in normal men", The Lancet, vol. 336, Oct. 20, 1990, pp. 955-959 and 1517-1518.

C. G. Francisco, et al., "Long-acting contraceptive agents: testosterone esters of unsaturated acids", Steroids, Jan. 1990, vol. 55, Butterworths.

John M. Hoberman and Charles E. Yesalis, "The History of Synthetic Testosterone", Scientific American, Feb. 1995, pp. 76-81.

Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano[3,2-g]quinolin-2-one. Bioorg. Med. Chem. Lett., 9: 1003, 1999.

Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335,1999.

Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210, 1999.

Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.

Dalton JT, Mukherjee A, Zhu Z, Kirkovsky L, and Miller DD. Discovery of Nonsteroidal Androgens. Biochem. Biophys. Res. Commun.,244(1):1-4, 1998.

Edwards JP, West SJ, Pooley CLF, Marschke KB, Farmer LJ, and Jones TK. New nonsteroidal androgen receptor modulators based on 4-(trifluoromethyl)-2-(1H)-Pyrololidino[3,2-g]quinolone. Bioorg. Med. Chem. Lett., 8: 745, 1998.

Buchwald, et Long-term, continuous intravenous heparin administration by an implantable infusion pump in ambulatory patients with recurrent venous thrombosis.Surgery. 1980 88(4):507-16.

Wahner, et al (1984) "Assesment of Bone Mineral Part 1" J Nucl. Medicine, 1134-1141.

Wahner, et al (1985) "Bone Mineral Density of the Radius" J. Nucl Medicine 26 13-39.

Faulkner KG, et al (1991) "Noninvasive measurements of bone mass, structure, and strength: current methods and experimental techniques." Am J Rosentgenology 157:1229-1237.

Hanada, K., et al (2003) "Bone anabolic effects of S-40503, a novel nonsteroidal selective androgen receptor modulator (SARM), in rat models of osteoporosis." Biol. Pharm. Bull. 26:1563-1569.

Kalu, DN, (1991) "The ovariectomized rat model of postmenopausal bone loss. Bone Miner." 15" 75-91.

Narayanan, et al "Steroidal Androgens and Nonsteroidal, Tissue Selective Androgen Receptor Modulators (SARM) Regulate Androgen Receptor Function Through Distinct Genomic and Non-Genomic Signaling Pathways." The Endocrine Society—Programs and Abstracts—89$^{th}$ Annual Meeting—Paper P1-595.

Yepuru, et al "An Angrogen Receptor-b Specific Selective Estrogen Receptor Modulator (SERM) Inhibits the Growth of the Prostate Cancer Cells and Stromal-Epithilial Tumor Xenograft." The Endocrine Society—Programs and Abstracts—89$^{th}$ Annual Meeting—Paper OR6-3.

Dalton, et al "Therapeutic Promise of Selective Androgen Receptor Modulators (SARSs): Preclinical and Clinical Proof-of-Concept Studies." The Endocrine Society—Programs and Abstracts—89$^{th}$ Annual Meeting—Paper S41-2.

Matsumoto, "Hormonal terapy of male hypogonadism" Endocrinol. Met. Clin. N. Am.: 23:857-75 (1994).

Zhou et al., Molec. Endocrinol. 9: 208-18 (1995).

Sundaram et al., "7 Alpha-Methyl-Nortestosterone (MENT): The Optimal Androgen for Male Contraception", Ann. Med., 25:199-205 (1993).

Wahner H W et al., "Assesment of Bone Mineral Part 1", J Nucl Medicine, pp. 1134-1141 (1984).

Wahner H W et al., "Bone Mineral Density of the Radius", J Nucl Medicine, 26:13-39 (1985).

Singh et al., "Androgens stimulate myogenic differentiation and inhibit adipogenesis in C3H 10T1/2 pluripotent cells through an androgen receptor-mediated pathway" Endocrinology,144(11):5081-8, Jul. 24, 2003.

Langer, "New methods of drug delivery", Science 249:1527-1533(1990).

Treat et al., in Liposomes in the Therapy of infections disease and cancer, Lopez-Berestein and Fidler (eds.), Liss New York, pp. 353-365 (1989).

Sefton, "Implantable pumps" CRC Crit. Ref. Biomed. Eng. 14:201 (1987).

Campfield et al., 1995, "Recombinant mouse OB protein: evidence for a peripheral signal linking adiposity and central neural networks" Science 269:546-549.

Dalton et al., "Therapeutic Promise of Selective Androgen Receptor Modulators (SARSs): Preclinical and Clinical Proof-of-Concept Studies"—The Endocrine Society—Programs and Abstracts—89$^{th}$ Annual Meeting—Paper S41-2.

Goodson, in Medical Applications of controlled Release, supra, vol. 2, pp. 115-138 (1984).

Narayanan et al., "Steroidal Androgens and Nonsteroidal, Tissue Selective Androgen Receptor Modulators (SARM) Regulate Androgen Receptor Function Through Distinct Genomic and Non-Genomic Signaling Pathways" The Endocrine Society—Programs and Abstracts—89$^{th}$ Annual Meeting—Paper P1-595.

Edwards, J. P. et al., Bio. Med. Chem. Let., 9, 1003-1008(1999).

Pelleymounter et al., 1995, "Effects of the Obese gene product on body weight regulation in ob/ob mice", Science 269:540-543.

Steinberger et al., Effect of chronic Administration of Testosterone Enanthateon Sperm Production and Plasma Testosterone, Follicle Stimulating Hormone, and Luteinizing Hormone Levels: a Preliminary Evaluation of possible Male Contraceptive, Fertility and Sterility 28:1320-28 (1977).

World Health Organization Task Force on Methods and Regulation of Male Fertility "Contraceptive Efficacy of Testosterone-Induced Azoospermia and Oligospermia in Normal Men", Fertility & Sterility 65:821-29 (1996).

Wu, "Effects of Testosterone Enanthate in Normal Men: Experience from a Multicenter contraceptive efficacy study", Fertility and Sterility 65:626-36 (1996).

International Search Report of Application No. PCT/US08/04816 issued on Jul. 8, 2008.

International Search Report of Application No. PCT/US05/19788 issued on Jun. 16, 2006.

Georgian Search Report of Application No. AP 2005 009805 issued on Jan. 23, 2008.

Supplementary European Search Report of Application No. EP 05 75 8756 issued on May 29, 2008.

Kalu, DN (1991) "The ovariectomized rat model of postmenopausal bone loss Bone Miner" 15:175-91.

Considine et al., 1995, "Evidence against either a premature stop codon or the absence of obese gene Mrna in human obesity", J. Clin. Invest. 95:2986-2988.

Tucker et al "Nonsteroidal antiandrogens. Synthesis and structure-activity relationships of 3-substituted derivatives of 2-hydroxypropionanilides." *J. Med Chem* (1988), 31, 954-959.

Buchwald et al. "Long-term, continuous intravenous heparin administration by an implantable infusion pump in ambulatory patients with recurrent venous thrombosis."Surgery 88:507 (1980).

Saudek et al."A preliminary trial of the programmable implantable medication system for insulin delivery." N. Engl. J. Med. 321:574 (1989).

Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.

Kirkovsky et al., "Approaches to Irreversible non-steroidal chiral antiandrogen", Department of Pharmaceutical Sciences, University of Tennessee, 47th Southeast/51st Southeast Joint Regional Meeting of the American Chemical Society, Memphis, TN, Nov. 29-Dec. 1, 1995.

Berger et al., "Concepts and Limitations in the application of radiolabeled antiandrogens, estrogens, or androgen as isotropic scanning agents for the prostate", Invest. Urol, (1975), 1391, 10-16.

Tucker and Chesterson, J. Med Chem. 1988, 31, pp. 885-887, "Resolution of the Nonsteroidal Antiandrogen-4'-Cyano-3-[(4-fluorophenyl)sulfonyl]-2-hydroxy-2-methyl-3'-(trifluoromethyl)-propionanilide and the Determination of the Absolute Configuration of the Active Enantiomer".

Wu, "Male Contraception: Current Status and Future Prospects", Clinical Endocrinology, (1988), 29, pp. 443-465.

David J. Handelsman, "Bridging the gender gap in contraception: another hurdle cleared" The Medical Journal of Australia, vol. 154, Feb. 18, 1996, pp. 230-233.

Edwards JP, Higuchi RI, Winn DT, Pooley CLF, Caferro TR, Hamann LG, Zhi L, Marschke KB, Goldman ME, and Jones TK. Nonsteroidal androgen receptor agonists based on 4-(trifluoromethyl)-2H-pyrano [3, 2-g]quinolin-2-one. Bioorg. Med. Chem. Lett., 9: 1003, 1999.

Mukherjee A, Kirkovsky L, Yao XT, Yates CR, and Dalton JT. Enantioselective Binding of Casodex to the Androgen Receptor. Xenobiotica 26(2): 117-122, 1996.

Dalton JT, Mukherjee A, Zhu Z, Kirkovsky L; and Miller DD. Discovery of Nonsteroidal Androgens. Biochemical and Biophysical Research Communications, 244(1): 1-4, 1998.

Mukherjee A, Kirkovsky LI, Kimura Y, Marvel MM, Miller DD, and Dalton JT. Affinity Labeling of the Androgen Receptor with Nonsteroidal Chemoaffinity Ligands. Biochemical Pharmacology, 58: 1259-1267, 1999.

Kirkovsky L, Mukherjee A, Yin D, Dalton JT, and Miller DD. Chiral Nonsteroidal Affinity Ligands for the Androgen Receptor. 1. Bicalutamide Analogs bearing Electrophilic Groups at the Aromatic Ring B. Journal of Medicinal Chemistry, 43: 581-590, 2000.

Marhefka CA, Moore IIBM, Bishop TC, Kirkovsky L, Mukherjee A, Dalton JT, Miller DD. Homology Modeling Using Multiple Molecular Dynamics Simulations and Docking Studies of the Human Androgen Receptor Ligand Binding Domain Bound to Testosterone and Nonsteroidal Ligands. Journal of Medicinal Chemistry, 44: 1729-1740, 2001.

He Y, Yin D, Perera MA, Kirkovsky L, Stourman N, Dalton JT, and Miller DD. Novel Nonsteroidal Ligands with High Affinity and Potent Functional Activity for the Human Androgen Receptor. European Journal of Medicinal Chemistry, 37: 619-634, 2002.

Yin D, He YS Hong SS, Marhefka CA, Stourman N, Kirkovsky L, Miller DD, and Dalton JT. Key Structural Features of Nonsteroidal Ligands for Binding and Activation of the Androgen Receptor. Molecular Pharmacology, 63:211-223, 2003.

Yin D, Xu H, He Y, Kirkovsky L, Miller DD, and Dalton JT. Pharmacology, Pharmacokinetics and Metabolism of Acetothiolutamide, A Novel Nonsteroidal Agonist for the Androgen Receptor. Journal of Pharmacology and Experimental Therapeutics, 304(3):1323-1333, 2003.

Yin D, Gao W, Kearbey JD, Xu H, Chung K, Miller DD, and Dalton JT. Pharmacodynamics of Selective Androgen Receptor Modulators. Journal of Pharmacology and Experimental Therapeutics, 304(3): 1334-1340, 2003.

Wu Z, Gao W, Phelps M, Wu D, Miller DD, and Dalton JT. The Favorable Effects of Weak Acids on Negative-Ion Electrospray Mass Spectrometry. Analytical Chemistry, 76(3):839-847, 2004.

Kearbey, J. D., Wu, D., Gao, W., Miller, D. D., and Dalton, J. T. (2004). Pharmacokinetics of S-3-(4-acetylamino-phenoxy)-2-hydroxy-2-methyl-N-(4-nitro-3-trifluoromethyl-phenyl)-propionamide in rats, a non-steroidal selective androgen receptor modulator. Xenobiotica 34(3), 273-80.

Marhefka, C. A., Gao, W., Chung, K., Kim, J., He, Y., Yin, D., Bohl, C., Dalton, J. T., and Miller, D. D. (2004). Design, synthesis, and biological characterization of metabolically stable selective androgen receptor modulators. *J Med Chem* 47(4), 993-8.

Bohl CE, Chang C, Mohler ML, Miller DD, Swaan PW, and Dalton JT. A Ligand-Based Approach to Identify Quantitative Structure-Activity Relationships for the Androgen Receptor. Journal of Medicinal Chemistry, 47(15):3765-3776, 2004.

Gao, W., Kearbey, J.D., Nair, V.A., Chung, K., Parlow, A.F., Miller, D.D., and Dalton, J.T. Comparison of the Pharmacological Effects of a Novel Selective Androgen Receptor Modulator (SARM), the 5{alpha}-Reductase Inhibitor Finasteride, and the Antiandrogeo Hydroxyflutamide in Intact Rats: New Approach for Benign Prostate Hyperplasia (BPH). Endocrinology, 145(12): 5420-5428, 2004.

Nair VA, Mustafa $SM_3$ Mohler ML, Fisher SJ, Dalton JT, and Miller DD. Synthesis of Novel Iodo Derived Bicalutamide Analogs. Tetrahedron Letters, 45: 9475-9477, 2004.

Chen J, Hwang DJ, Bohl CE, Miller DD, and Dalton JT. A Selective Androgen Receptor Modulator (SARM) for Hormonal Male Contraception. Journal of Pharmacology and Experimental Therapeutics, 312(2): 546-553,2005.

Nair V, Mustafa SM, Mohler ML, Fisher S J, Dalton JT, and Miller DD. Synthesis of irreversibly binding bicalutamide analogs for imaging studies. Tetrahedron Letters. 46:4821-4823, 2005.

Bohl CE, Gao W, Miller DD, Bell CE, Dalton JT. Structural Basis for Antagonism and Resistance of Bicalutamide in Prostate Cancer. Proc Natl Acad Sci USA. 102(17): 6201-6206, 2005.

Chen J, Kim J, and Dalton JT. Discovery and Therapeutic Promise of Selective Androgen Receptor Modulators. Molecular Interventions, 5(3):173-188, 2005.

Kim J, Wu D, Hwang DJ, Miller DD, and Dalton JT. The 4-Para-Substituent of S-3-(Phenoxy)-2-hydroxy-2-methyl-N-(4-nitro-3-trifluoromethyl]-phenyl)-propionamides is a Major Structural Determinant of In Vivo Disposition and Activity of Selective Androgen Receptor Modulators. Journal of Pharmacology and Experimental Therapeutics, 315(I):230-239, 2005.

Gao W, Reiser PJ, Coss CC, Phelps MA, Kearbey JD, Miller DD, and Dalton JT. Selective Androgen Receptor Modulator (SARM) Treatment Improves Muscle Strength and Body Composition, and Prevents Bone Loss in Orchidectomized Rats. Endocrinology, 146(11):48B7-4897, 2005.

Bohl CE, Miller DD, Chen J, Bell CE, and Dalton JT. Structural Basis for Accomodation of Nonsteroidal Ligaiids in the Androgen Receptor. Journal of Biological Chemistry, 280(45):37747-37754, 2005.

Gao W, Bohl CE, and Dalton JT. Chemistry and structural biology of androgen receptor. Chemical Reviews, 1G5(9):3352-70,2005.

Chen J, Hwang DJ, Chung K, Bohl CE, Fisher SJ, Miller DD, Dalton JT. In vitro and in vivo structure-activity relationships of novel androgen receptor ligands with multiple substituents in the B-ring. Endocrinology, 146(12):5444-54, 2005.

Segal S, Narayanan R, Dalton JT. Therapeutic potential of the SARMs: revisiting the androgen receptor for drug discovery. Expert Opinion in Investigational Drugs. 15(4):377-87, 2006.

Gao W, Johnston JS, Miller DD, Dalton JT. Inter-Species Differences in Pharmacokinetics and Metabolism of S-3-(4-acelylamino-phenoxy)-2-hydroxy-2-methyl-N-(4-nitro- 3-trifluoromethyi-phenyl>propionamide: The Role of N-Acetyltransferase. Drug Metabolism and Disposition, 34(2):254-260, 2006.

Gao W, Wu Z, Bohl CE, Yang J, Miller DD, Dalton JT. Characterization of the In vitro Metabolism of Selective Androgen Receptor Modulator (SARM) Using Human, Rat and Dog Liver Enzyme Preparations. Drug Metabolism and Disposition, 34(2):243-253, 2006.

Wu D, Wu Z, Yang J, Nair VA, Miller DD, Dalton JT. Pharmacokinetics and metabolism of a selective androgen receptor modulator (SARM) in rats-implication of molecular properties and intensive metabolic profile to investigate ideal pharmacokinetic characteristics of a propanamide in preclinical study. Drug Metabolism and Disposition, 34(3):483-494, 2006.

Yang J, Bohl CE, Nair VA, Mustafa SM, Hong SS, Miller DD, Dalton JT. Preclinical pharmacology of a nonsteroidal ligand for androgen receptor mediated imaging of prostate cancer. Journal of Pharmacology and Experimental Therapeutics, 317(I):402-408, 2006.

Gao W, Kim J, Dalton JT, Pharmacokinetics and Pharmacodynamics of Nonsteroidal Androgen Receptor Ligands. Pharmaceutical Research, 23(8):1641-165B, 2006.

Hwang DJ, Yang J, Xu H, Rakov IM, Mohler ML, Dalton JT, Miller DD—Aryl isothiocyanato selective androgen receptor modulators (SARMs) for prostate cancer. Bioorganic and Medicinal Chemistry, , 14(19):6525-6538, 2006.

Bhasin S, Calof OM, Storer TW, Lee ML, Mazer NA, Jasuja R, Montori VM, Gao W, Dalton JT. Drug insight: Testosterone and selective androgen receptor modulators as anabolic therapies for chronic illness and aging. Nature, Clinical Practice in Endocrinology and Metabolism, 2(3): 146-159,2006.

Nair VA; Mustafa SM; Mohler ML; Dalton JT; Miller DD.Synthesis of oxazolidinedione derived bicalutamide analogs . Tetrahedron Letters, 47 (23): 3953-3955, 2006.

Patil R, Li W, Ross CR, Kraka E, Cremer D, Mohler ML, Dalton JT, and Miller DD. Cesium fluoride and tetra-n-butylammonium fluoride mediated 1,4-N-O shift of disubstituted phenyl ring of a bicalutamide derivative. Tetrahedron Letters, 47:3941-3944, 2006.

Kearbey JD, Gao W, Narayanan R, Fisher SJ, Wu D, Miller DD, Dalton JT. Selective Androgen Receptor Modulator (SARM) Treatment Prevents Bone Loss and Reduces Body Fat in Ovariectomized Rats. Pharmaceutical Research, 24(2):328-335, 2006.

Bohl CE, Wu Z, Miller DD, Bell CE, Dalton JT. Crystal structure of the TS77A human androgen receptor Ugand-binding domain completed to cyproterone acetate provides insight for ligand-induced conformational changes and structure-based drug design. Journal of Biological Chemistry, 282(18):13648-13655,2007.

Gao W, Dalton JT, Expanding the therapeutic use of androgens via selective androgen receptor modulators (SARMs). Drug Discovery Today, 12(5-6):241-248, 2007.

Gao W, Dalton JT. Ockham's razor and selective androgen receptor modulators (SARMs): are we overlooking the role of 5a-reductase? Molecular Interventions, 7(1):1Q-13, 2007.

Sharifi N, Hamel E, Lill MA, Risbood P, Kane CT Jr, Hossain $MT_3$ Jones A, Dalton JT, Farrar WL. A bifunctional colchicinoid that binds to the androgen receptor. Molecular Cancer Therapeutics, 6(8):2328-2336, 2007.

Bisson WH, Cheltsov $AV_5$ Bruey-Sedano N, Lin B, Chen J, Goldberger N, May LT, Christopoulos A, Dalton JT, Sexton PM, Zhang XK, Abagyan R. Discovery of antiandrogen activity of nonsteroidal scaffolds of marketed drugs. Proceedings of the National Academy of Sciences, U S A. 104(29): 1192741932, 2007.

Mukherjee A, Kirkovsky L, Marvel M, Miller DD, and Dalton JT, Development of Nonsteroidal Androgen Receptor Ligands for Imaging Prostate Tumors. PharmSci, 1(1):S-681, 1998.

Yin D, Kirkovsky L, Stourman N, Miller DD, and Dalton JT. In Vitro Pharmacology and In Vivo Pharmacokinetics of (R)-Para-Acetamido-Bicalutamide. PharmSci, 1(4):S-3185, 1999.

Gao W, Chung K, Miller DD, and Dalton JT. In Vitro Metabolism and In Vivo Tissue Selectivity of Andarine. PharmSci 4(4): 2002.

Perera MA, Yin D, Chung K, Miller DD, and Dalton JT. Pharmacokinetics and Allometric Scaling of Andarine. PharmSci 4(4): 2002.

Xu H, Chung K, Hwang DJ, Miller $DD_7$ and Dalton JT. Pharmacodynamics of Electrophilic Androgen Receptor Ligands in Prostate Cancer Cell Lines. PharmSci 4(4): 2002.

Wang L, Miller DD, and Dalton JT, Androgen Receptor Mediated Transcriptional Activation of SARMs is Enhanced by Nuclear Receptor Coactivators. The Endocrine Society, Philadelphia, Jun. 2003, Abstract #P2-95.

Gao W, Kearbey JD, Chung K, Miller DD, and Dalton JT. Pharmacologic Effects of a Novel Selective Androgen Receptor Modulator (SARM), Flutamide and Finasteride in Intact Male Rats. The Endocrine Society, Philadelphia, Jun. 2003, Abstract #P3-221.

Kim J, Hwang DJ, Miller DD, and Dalton JT. In vitro and In vivo Pharmacologic Activity of 4-Halo Substituted SARMs. The Endocrine Society, Philadelphia, Jun. 2003, Abstract #P3-198.

Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335, 1999.

Dalton JT, et al "Pharmacokinetics of Aminolevulinic Acid after Oral and Intravenous Dosing in Dogs." Drug Metabolism and Disposition, 27 (4):432-435, 1999.

Grundy, Metabolic and health complications of obesity, 1990, Disease-a-Month 36:Dec.; 36(12):641-731.

Halaas et al., 1995, "Weight-reducing effects of the plasma protein encoded by the obese gene", Science 269:543-546.

Hamilton et al., 1995 "Increased obese mRNA expression in omental fat cells from massively obese humans", Nature Med., 1:953.

Kim J, Hwang DJ, Rakov I, Miller DD, and Dalton JT. Structure-Activity Relationships for Modification of the Linkage Group and B-Ring of Selective Androgen Receptor Modulators. The AAPS Journal, vol. 7(S2):T2117,2005.

Hwang DJ, Yang J, Mohler ML, Dalton JT, Miller DD.Synth.esis and testing of both reversible and irreversible selective androgen receptor modulators (SARMs) for prostate cancer. Abstracts of Papers of the American Chemical Society, 231: 274-MEDI, Mar. 26, 2006.

Narayanan R, Bohl CE, Kearbey JD, Coss CC, Miller DD, and Dalton JT. Molecular Mechanism for the Tissue Selectivity of a Novel Non-Steroidal Selective Androgen Receptor Modulator. Genome-Wide Mapping of Androgen Receptor Binding Sites, The Endocrine Society, Boston, Abstract # OR49-1, Jun. 2006.

Narayanan R, Coss CC, Yepuru MM, Miller DD and Dalton JT. Steroidal Androgens and Nonsteroidal, Tissue Selective Androgen Receptor Modulators (SARM) Regulate Androgen Receptor Function Through Distinct Genomic and Non-Genomic Signaling Pathways. The Endocrine Society, Toronto, Abstract #PI-595, Jun. 2007.

Gao W, Reiser PJ, Kearbey JD, Phelps MA, Coss $CC_7$ Miller DD, and Dalton JT. Effects of a Novel Selective Androgen Receptor Modulator (SARM) on Skeletal Muscle Mass and Strength in Castrated Male Rats. The Endocrine Society, New Orleans, Abstract # P2-120, Jun. 2005.

Wu D, Wu Z, Nair V, Miller DD, and Dalton JT—Urinary Metabolites of S-I, A Novel Selective Androgen Receptor Modulator (SARM), in Rats. The AAPS Journal, vol. 6, No. 4, Abstract #W53OO, Nov. 2004.

Fisher SJ, Hong SS, Miller DD, and Dalton JT. Preclinical Pharmacology and Pharmacokinetics of a Novel A-ring Substituted Selective Androgen Receptor Modulator (SARM) in Rats. The AAPS Journal, vol. 6, No. 4, Abstract #T2256, Nov. 2004.

Bohl CE, Chang C, Mohler M, Miller DD, Swaan PW, and Dalton JT. A Ligand-based Approach to Identify Quantitative Structure Activity Relationships for the Androgen Receptor. The AAPS Journal, vol. 6, No. 4, Abstract #W4111, Nov. 2004.

Hwang DJ, Chen JY, Kim J, Dalton JT, Miller DD. Synthesis and biological testing of (2S)-multU halogenated B-ring 2-hydroxy-2-methylpropionamide selective androgen receptor modulators (SARMs): Probing the B-ring pocket. Abstracts of Papers of the American Chemical Society, 229: U140-U140 176—MEDI Part 2, Mar. 13, 2005.

Hwang DJ, Chen JY, Xu HP, Mustafa SM, Dalton JT, Miller DD. Synthesis of isothiocyanate derivatives of irreversible selective androgen receptor modulators (SARMs) and biological testing in prostate cancer cell lines. Abstracts of Papers of the American Chemical Society, 229: U140-U140 177—MEDI Part 2, Mar. 13, 2005.

Gao W, Stuart LB, Yates CR, Miller DD, and Dalton JT. Regulation of Cytochrome P450s by Selective Androgen Receptor Modulators (SARMs) in Primary Culture of Human Hepatocytes.). PharmSci 5 (4): T3338,2003.

Gao W, Veverka KA, Chung K, Miller DD, and Dalton JT. Species Difference in the Metabolism of Selective Androgen Receptor Modulators (SARMs). PharmSci 5 (4): T3336, 2003.

Kearbey JD, Gao W, Miller DD, and Dalton JT. Selective androgen receptor modulators inhibit bone resorption in rats. PharmSci 5 (4): R6167, 2003.

Xu H, Hwang DJ, Miller DD, and Dalton JT. In Vitro and In Vivo Anticancer Activity of S-NTBA for Prostate Cancer. PharmSci 5 (4): T2378, 2003.

U.S. Appl. No. 10/683,156, filed Oct. 14, 2003, Dalton, James T. et al.

U.S. Appl. No. 10/861,923, Dalton, James T. et al.

Non Final Rejection mailed Nov. 30, 2006 in U.S. Appl. No. 11/146,247.

Final Rejection mailed May 14, 2007 in U.S. Appl. No. 11/146,247.

Non Final Rejection mailed Oct. 5, 2007 in U.S. Appl. No. 11/146,247.

Non Final Rejection mailed Jul. 10, 2008 in U.S. Appl. No. 11/146,247.

Non Final Rejection mailed Feb. 6, 2009 in U.S. Appl. No. 11/146,247.

Notice of Allowance mailed Jul. 10, 2009 in U.S. Appl. No. 11/146,247.

Non Final Rejection mailed May 31, 2007 in U.S. Appl. No. 11/505,499.

Final Rejection mailed Jan. 3, 2008 in U.S. Appl. No. 11/505,499.

Non Final Rejection mailed Jul. 25, 2008 in U.S. Appl. No. 11/505,499.

Final Rejection mailed Mar. 20, 2009 in U.S. Appl. No. 11/505,499.

Advisory Action mailed Jun. 1, 2007 in U.S. Appl. No. 11/505,499.

Notice of Allowance mailed Aug. 11, 2009 in U.S. Appl. No. 11/505,499.

U.S. Appl. No. 12/484,551, filed Jun. 15, 2009, University of Tennessee Research Foundation.

TREATING WASTING DISORDERS WITH SELECTIVE ANDROGEN RECEPTOR MODULATORS

CROSS-REFERENCE TO RELATED APPLICATIONS

This application is a Continuation-In-Part of U.S. patent application Ser. No. 11/146,427, filed Jun. 7, 2005 now U.S. Pat. No. 7,622,503, which is a Continuation-In-Part Application of U.S. patent application Ser. No. 10/961,380, filed Oct. 12, 2004, which claims priority from U.S. Provisional Application Ser. No. 60/510,138, filed Oct. 14, 2003; U.S. patent application Ser. No. 10/861,923 filed Jun. 7, 2004, which is a Continuation-In-Part Application of U.S. patent application Ser. No. 10/310,150, filed Dec. 5, 2002 now U.S. Pat. No. 7,547,728, which claims priority of U.S. Provisional Application Ser. No. 60/336,185, filed Dec. 6, 2001; and U.S. patent application Ser. No. 10/863,524, filed Jun. 9, 2004, which is a Continuation-In-Part Application of U.S. patent application Ser. No. 10/371,213 filed Feb. 24, 2003 now U.S. Pat. No. 7,026,500, which is a Continuation-In-Part Application of U.S. patent application Ser. No. 10/270,232 filed Oct. 15, 2002 now U.S. Pat. No. 6,838,484, which is a Continuation-In-Part Application of U.S. patent application Ser. No. 09/935,045 filed Aug. 23, 2001 now U.S. Pat. No. 6,569,896, which claims priority of U.S. Provisional Application Ser. No. 60/300,083 filed Jun. 25, 2001 and U.S. Provisional Application Ser. No. 60/367,355 filed Aug. 24, 2000, all of which are hereby incorporated by reference.

GOVERNMENT INTEREST STATEMENT

This invention was made in whole or in part with government support under grant number R29 CA068096 awarded by the National Cancer Institute, National Institute of Health, and under grant number R15 HD35329, awarded by the National Institute of Child Health and Human Development, National Institute of Health. The government may have certain rights in the invention.

FIELD OF INVENTION

This invention relates to the prevention and treatment of wasting disorders with a selective androgen receptor modulator (SARM). More particularly, this invention relates to a method of treating, preventing, suppressing, inhibiting, or reducing the incidence of a wasting in a subject suffering from a muscle wasting disorder, by administering to the subject a selective androgen receptor modulator (SARM) compound and/or its analog, derivative, isomer, metabolite, pharmaceutically acceptable salt, pharmaceutical product, hydrate, N-oxide, prodrug, polymorph, impurity or crystal, or any combination thereof.

BACKGROUND OF THE INVENTION

Wasting refers to catabolism and/or the progressive loss of weight in a subject, or to loss of muscle mass and/or its progressive weakening and degeneration. Sarcopenia and cachexia are clinical manifestations of wasting. Wasting may be due to a chronic or acute condition (i.e. persisting over a long period of time) and may be associated with neurological, genetic or infectious pathologies, diseases, illnesses or conditions.

Wasting may be associated with Cachexias such as Cardiac Cachexia, AIDS Cachexia and Cancer Cachexia, malnutrition, Leprosy, Tuberculosis, Diabetes, Renal Disease, Chronic Obstructive Pulmonary Disease (COPD), Cancer, end stage Renal failure, Andropause, Frailty, Emphysema, Osteomalacia, HIV Infection, AIDS, or Cardiomyopathy.

In addition, other circumstances and conditions are linked to and can cause wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, long term hospitalization due to illness or injury, and alcoholism.

Wasting may include muscle wasting, for example as occurs with Muscular Dystrophies such as Duchenne Muscular Dystrophy and Myotonic Dystrophy; Muscle Atrophies such as Post-Polio Muscle Atrophy (PPMA), disuse deconditioning that occurs when a limb is immobilized, and/or sarcopenia.

If left unabated, wasting can have dire health consequences. For example, the changes that occur during wasting can lead to a weakened physical state that is detrimental to an individual's health, resulting in increased susceptibility to infection, or other diseases or conditions. In addition, muscle wasting is a strong predictor of morbidity and mortality in patients suffering from cachexia and AIDS. Innovative approaches are urgently needed at both the basic science and clinical levels to prevent and treat wasting disorders, in particular muscle wasting disorders.

SUMMARY OF THE INVENTION

This invention provides a method of treating a human subject suffering from a wasting disorder, or preventing, suppressing, inhibiting or reducing the incidence of a wasting disorder in a subject, comprising the step of administering to said subject a selective androgen receptor modulator (SARM) compound of formula XX:

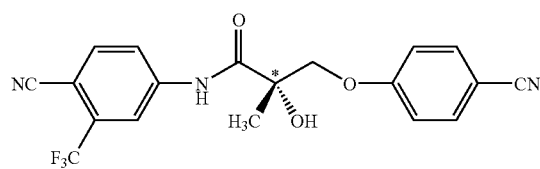

and/or its analog, derivative, isomer, metabolite, pharmaceutically acceptable salt, pharmaceutical product, hydrate, N-oxide, or any combination thereof.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention provides a method of treating a human subject suffering from a wasting disorder, or preventing, suppressing, inhibiting or reducing the incidence of a wasting disorder in a subject, comprising the step of administering to said subject a selective androgen receptor modulator (SARM) compound of formula XX:

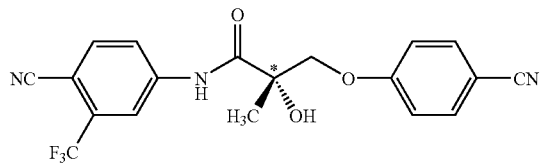

and/or its analog, derivative, isomer, metabolite, pharmaceutically acceptable salt, pharmaceutical product, hydrate, N-oxide, or any combination thereof.

In one embodiment, the methods of this invention provide for use of an analog, derivative, isomer, metabolite, pharmaceutically acceptable salt, pharmaceutical product, hydrate, N-oxide, prodrug, polymorph, impurity or crystal or combinations thereof of the SARM. In one embodiment, the methods of this invention provide for use of an analog of the SARM compound. In another embodiment, the methods of this invention provide for use of a derivative of the SARM compound. In another embodiment, the methods of this invention provide for use of an isomer of the SARM compound. In another embodiment, the methods of this invention provide for use of a metabolite of the SARM compound. In another embodiment, the methods of this invention provide for use of a pharmaceutically acceptable salt of the SARM compound. In another embodiment the methods of this invention provide for use of a pharmaceutical product of the SARM compound. In another embodiment, the methods of this invention provide for use of a hydrate of the SARM compound. In another embodiment the methods of this invention provide for use of an N-oxide of the SARM compound. In another embodiment, the methods of this invention provide for use of a prodrug of the SARM compound. In another embodiment, the methods of this invention provide for use of a polymorph of the SARM compound. In another embodiment, the methods of this invention provide for use of a crystal of the SARM-compound. In another embodiment, the methods of this invention provide for use of an impurity of the SARM compound. In another embodiment, the methods of this invention provide for use of a composition comprising a SARM compound, as described herein, or, in another embodiment, a combination of an analog, derivative, isomer, metabolite, pharmaceutically acceptable salt, pharmaceutical product, hydrate, N-oxide, prodrug, polymorph, impurity or crystal of the SARM.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the SARM compound. It will be appreciated by those skilled in the art that the SARMs for use in the methods of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the treatment of the conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of "pharmaceutically acceptable salts" of the SARMs, which may be produced, in one embodiment, using an amino-substituted SARM and an organic and inorganic acids, for example, citric acid and hydrochloric acid. Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

The invention also includes use of N-oxides of the amino substituents of the SARMs described herein. This invention provides for use of derivatives of the SARM compounds. In one embodiment, "derivatives" includes but is not limited to ether derivatives, acid derivatives, amide derivatives, ester derivatives and the like. In another embodiment, this invention further includes use of hydrates of the SARM compounds. In one embodiment, "hydrate" includes but is not limited to hemihydrate, monohydrate, dihydrate, trihydrate and the like.

This invention provides, in other embodiments, use of metabolites of the SARM compounds. In one embodiment, "metabolite" means any substance produced from another substance by metabolism or a metabolic process.

This invention provides, in other embodiments, use of pharmaceutical products of the SARM compounds. The term "pharmaceutical product" refers, in other embodiments, to a composition suitable for pharmaceutical use (pharmaceutical composition), for example, as described herein.

The SARM compounds for use according to the methods of the present invention can be classified as partial AR agonist/antagonists. The SARMs are AR agonists in some tissues, to cause increased transcription of AR-responsive genes (e.g. muscle anabolic effect). In other tissues, these compounds serve as competitive inhibitors of testosterone/DHT on the AR to prevent agonistic effects of the native androgens. In one embodiment, the SARM will have antagonist activity in a gonad of a subject, and agonist activity peripherally, such as, for example, in muscle. Such activity was demonstrated herein, in terms of the lack of androgenic effect in terms of sebaceous gland stimulation, yet anabolic effects, in terms of increased lean and diminished fat composition in subjects treated with the SARM.

In one embodiment the SARM used in the methods of this invention are part of a composition, which is a pharmaceutical composition, which, in another embodiment is a pellet, a tablet, a capsule, micronized and non-micronized capsule, a solution, a suspension, an emulsion, an elixir, a gel, a cream, a suppository or a parenteral formulation.

In one embodiment, the micronized capsules comprise particles containing a SARM of this invention, wherein the term "micronized" used herein refers to particles having a particle size is of less than 100 microns, or in another embodiment, less than 50 microns, or in another embodiment, less than 35 microns, or in another embodiment, less than 15 microns, or in another embodiment, less than 10 microns, or in another embodiment, less than 5 microns.

The pharmaceutical compositions may be administered in any effective, convenient manner including, for instance, administration by intravascular (i.v.), intramuscular (i.m.), intranasal (i.n.), subcutaneous (s.c.), sublingual, oral, rectal, intravaginal delivery, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

For administration to humans, according to the methods of this invention, it is expected that the physician will determine the actual dosage and duration of treatment, which will be most suitable for an individual and can vary with the age, weight and response of the particular individual. In one embodiment, the dosage may vary as a function of the genetic makeup of the subject to be treated.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any In one embodiment, the compositions of this invention may include, a SARM as described or any combination of the compounds thereof, together with one or more pharmaceutically acceptable excipients.

In one embodiment, "pharmaceutical composition" can mean a therapeutically effective amount of one or more compounds as described herein, including the SARM and/or SARMs, and other therapeutic molecules, as described herein, together with suitable excipients and/or carriers useful for the methods of this invention. In one embodiment, the compositions will comprise a therapeutically effective amount of a SARM and/or SARMs, as described. In one embodiment, the term "therapeutically effective amount" may refer to that amount that provides a therapeutic effect for a given condition and administration regimen. In one embodiment, such compositions can be administered by any method known in the art.

In one embodiment, the compositions for use in the methods of the present invention are formulated as oral or parenteral dosage forms, such as uncoated tablets, coated tablets, pills, capsules, powders, granulates, dispersions or suspensions. In another embodiment, the compositions for use in the methods of the invention are formulated for intravenous administration. In another embodiment, the compositions for use in the methods of the invention are formulated in ointment, cream or gel form for transdermal administration. In another embodiment, the compositions for use in the methods of the invention are formulated as an aerosol or spray for nasal application. In another embodiment, the compositions for use in the methods of the invention are formulated in a liquid dosage form. Examples of suitable liquid dosage forms include solutions or suspensions in water, pharmaceutically acceptable fats and oils, alcohols or other organic solvents, including esters, emulsions, syrups or elixirs, solutions and/or suspensions.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

The SARMs for use in the methods of this invention may be administered at various dosages. In one embodiment, the SARM is administered at a dosage of 0.1-200 mg per day. In one embodiment, the SARM is administered at a dose of 0.1-10 mg, or in another embodiment, 0.1-25 mg, or in another embodiment, 0.1-50 mg, or in another embodiment, 0.3-15 mg, or in another embodiment, 0.3-30 mg, or in another embodiment, 0.5-25 mg, or in another embodiment, 0.5-50 mg, or in another embodiment, 0.75-15 mg, or in another embodiment, 0.75-60 mg, or in another embodiment, 1-5 mg, or in another embodiment, 1-20 mg, or in another embodiment, 3-15 mg, or in another embodiment, 1-30 mg, or in another embodiment, 30-50 mg, or in another embodiment, 30-75 mg, or in another embodiment, 100-2000 mg.

The SARMs of this invention may be administered at various dosages. In one embodiment, the SARM is administered at a dosage of 1 mg. In another embodiment the SARM is administered at a dosage of 5 mg, or in another embodiment, 3 mg, or in another embodiment 10 mg, or in another embodiment 15 mg, or in another embodiment 20 mg, or in another embodiment 25 mg, or in another embodiment 30 mg, or in another embodiment 35 mg, or in another embodiment 40 mg, or in another embodiment 45 mg, or in another embodiment 50 mg, or in another embodiment 55 mg, or in another embodiment 60 mg, or in another embodiment 65 mg, or in another embodiment 70 mg, or in another embodiment 75 mg, or in another embodiment 80 mg, or in another embodiment 85 mg, or in another embodiment 90 mg, or in another embodiment 95 mg or in another embodiment 100 mg.

In one embodiment, the methods of this invention make use of the SARM as described at a dose as described herein, given orally, once a day.

The SARMs have been shown herein to be anabolic. In one embodiment, the SARMs are useful in treating, preventing, suppressing, delaying onset, reducing the incidence or reducing the severity of a wasting disease, condition or disorder in a subject.

A wasting disease, condition or disorder refers, in some embodiments as a disease condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein, protein catabolism at particular sites, etc., as will be appreciated by one skilled in the art.

In one embodiment, the wasting disease, condition or disorder is cachexia. Cachexia is, in some embodiments, weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass.

Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

Numerous other diseases may be associated with cachexia, any of which may be treated with the SARMs as described herein, and represent an embodiment of this invention.

In one embodiment, this invention provides use of the SARM compound or SARMs as described herein, or a prodrug, analog, isomer, metabolite, derivative, pharmaceutically acceptable salt, pharmaceutical product, polymorph, crystal, impurity, N-oxide, hydrate or any combination thereof, for 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; and/or 5) treating, preventing, inhibiting, reducing or suppressing muscle protein catabolism due to a muscle wasting disorder. In another embodiment, the invention provides a composition comprising the SARM for use in the methods as described herein.

In one embodiment, the invention provides a use of SARM compounds for treating a subject suffering from a muscle wasting disorder. In another embodiment, the use of a SARM compound for treating a subject suffering from a muscle wasting disorder includes administering a pharmaceutical composition including the SARM compound.

A muscle is a tissue of the body that primarily functions as a source of power. There are three types of muscles in the body: a) skeletal muscle the muscle responsible for moving extremities and external areas of the bodies; b) cardiac muscle—the heart muscle; and c) smooth muscle—the muscle that is in the walls of arteries and bowel.

In one embodiment, "muscle wasting" or "muscular wasting", used herein interchangeably, refers to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

In one embodiment, muscle wasting or wasting in a subject is a result of the subject having a muscular dystrophie; muscle atrophy; X-linked spinal-bulbar muscular atrophy (SBMA), cachexia; malnutrition, tuberculosis, leprosy, diabetes, renal disease, chronic obstructive pulmonary disease (COPD), cancer, end stage renal failure, burns, diabetes, congestive heart failure, sarcopenia, emphysema, osteomalacia, or cardiomyopathy.

In another embodiment, the muscle wasting, or wasting disorder is due to infection with enterovirus, Epstein-Barr virus, herpes zoster, HIV, trypanosomes, influenze, coxsackie, rickettsia, trichinella, schistosoma or mycobacteria.

The muscular dystrophies are genetic diseases characterized by progressive weakness and degeneration of the skeletal or voluntary muscles that control movement. The muscles of the heart and some other involuntary muscles are also affected in some forms of muscular dystrophy. The major forms of muscular dystrophy (MD) are: duchenne muscular dystrophy, myotonic dystrophy, duchenne muscular dystrophy, becker muscular dystrophy, limb-girdle muscular dystrophy, facioscapulhumeral muscular dystrophy, congenital muscular dystrophy, oculopharyngeal muscular dystrophy, distal muscular dystrophy and emery-dreifuss muscular dystrophy.

Sarcopenia is a debilitating disease that afflicts the elderly and chronically ill patients and is characterized by loss of muscle mass and function, which may be treated, etc., by the methods of this invention. In addition, other circumstances and conditions are linked to, and can cause muscle wasting disorders. For example, studies have shown that in severe cases of chronic lower back pain, there is paraspinal muscle wasting.

Muscle wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance. Such wasting may be treated, prevented, etc., with the administration of Compound XX as herein described.

Long term hospitalization due to illness or injury, or disuse deconditioning that occurs, for example, when a limb is immobilized, can also lead to wasting, such as, in one embodiment, muscle wasting. Studies have shown that in patients suffering injuries, chronic illnesses, burns, trauma or cancer, who are hospitalized for long periods of time, there is a long-lasting unilateral wasting and/or muscle wasting, with a consequent decrease in body mass, which may be treated or positively affected by the administration of Compound XX, representing other embodiments of the methods of this invention.

Injuries or damage to the central nervous system (CNS) are also associated with wasting and/or muscle wasting disorders. Injuries or damage to the CNS can be, for example, caused by diseases, trauma or chemicals. Examples are central nerve injury or damage, peripheral nerve injury or damage and spinal cord injury or damage. It is to be understood that any of these conditions may be treated or positively affected by the administration of Compound XX, and represent embodiments of the methods of this invention.

In another embodiment, wasting and/or muscle wasting may be a result of alcoholism, and may be treated with the compounds and compositions as described herein, representing embodiments of the methods of this invention.

In one embodiment, the methods of this invention promote increased muscle performance, muscle size, muscle strength, or any combination thereof in a subject. In another embodiment, the SARMs and compositions as herein described are useful in promoting or speeding recovery following a surgical procedure, which in turn represents an embodiment of this invention, in particular as this functions as a means of preventing a wasting disease or disorder, as herein described.

Increased lean body mass is associated with decreased morbidity and mortality for certain wasting and muscle-wasting disorders, which may be accomplished by administering Compound XX to a subject thereby afflicted, representing one embodiment of the invention. In another embodiment, the administration of the SARM/s, as herein described, promotes lean body mass in a subject, wherein the subject is elderly, or in another embodiment, is not elderly, and in one embodiment, is obese, or in another embodiment, has truncal obesity, or in another embodiment, has coronary artery disease, or in another embodiment, any form of atherosclerosis, or in another embodiment, diabetes, or in another embodiment, risk factors for any of the diseases listed herein.

In one embodiment, the present invention provides a use of a SARM compound for reducing a fat mass in a subject. In another embodiment the SARM compound is a prodrug, analog, isomer, metabolite, derivative, pharmaceutically acceptable salt, pharmaceutical product, polymorph, crystal, impurity, N-oxide, hydrate or any combination thereof, of Compound XX, or a composition comprising the same.

In another embodiment, this invention provides for the use of a SARM compound of this invention, such as one having the structure of formula XX or its prodrug, analog, isomer, metabolite, derivative, pharmaceutically acceptable salt, pharmaceutical product, polymorph, crystal, impurity, N-oxide, hydrate or any combination thereof, or a composition comprising the same, in treating obesity or diabetes associated with a metabolic syndrome in a subject In another embodiment, the subject has a hormonal imbalance, disorder, or disease. In another embodiment the subject has menopause, or in another embodiment, the subject has andropause, or age-related androgen decline in a male subject.

In one embodiment, the present invention provides a use of a SARM compound as described for increasing a lean mass in a subject. In one embodiment the subject has a hormonal imbalance, disorder, or disease. In another embodiment the subject has a disease listed herein, which is negatively impacted by obesity, or the presence of greater fat mass, or in another embodiment, is positively affected by the increase in lean mass in the subject.

In one embodiment, the disease or disorder is positively affected or treated with the SARM/s of this invention by increasing circulating or tissue levels of IGF-1, or in another embodiment, decreasing levels of SHBG, or in another embodiment, a combination thereof.

In another embodiment, this invention relates to a method of preventing, suppressing, inhibiting or reducing the incidence of obesity in a subject, comprising the step of administering to the subject a selective androgen receptor modulator (SARM) as herein described and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the incidence of obesity in the subject.

In one embodiment, the SARM compounds when administered, alter the levels of leptin in a subject. In another embodiment, the SARM compounds decrease the levels of leptin. In another embodiment, the SARM compounds increase the levels of leptin in a subject. In one embodiment, the SARM/s affect circulating, or in another embodiment, tissue levels of leptin. In one embodiment, the term 'level/s of leptin' refers to the serum level of leptin.

Since leptin is implicated in controlling appetite, weight loss, food intake, and energy expenditure, modulating and/or controlling the levels of leptin is a useful therapeutic approach in treating preventing, inhibiting or reducing the incidence of obesity in subjects suffering from obesity. Modulating the level of leptin can result in a loss of appetite, a reduction of food intake, and an increase in energy expenditure in the subject, and thus may contribute to the control and treatment of obesity.

The term "obesity" refers, in one embodiment, to an increase in body weight beyond the limitation of skeletal and physical requirement, as the result of excessive accumulation of fat in the body.

The term "obesity-associated metabolic disorder" refers, in one embodiment, to a disorder which results from, is a consequence of, is exacerbated by or is secondary to obesity. Non-limiting examples of such a disorder are osteoarthritis, Type II diabetes mellitus, increased blood pressure, stroke, and heart disease.

The term "diabetes", in one embodiment, refers to a relative or absolute lack of insulin leading to uncontrolled carbohydrate metabolism. Most patients can be clinically classified as having either insulin-dependent diabetes mellitus (IDDM or Type-I diabetes) or non-insulin-dependent diabetes mellitus (NIDDM or Type-II diabetes).

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In addition, androgens have been shown to be involved in commitment of mesenchymal pluripotent cells into myogenic lineage and to block differentiation into adipogenic lineage, which favors lean mass versus fat mass accumulation. In one embodiment, the SARM/s as described herein, similarly bias toward lean mass versus fat accumulation, which can be applied to any of the conditions for which the methods of this invention are applicable.

In another embodiment, this invention relates to a method of promoting, increasing or facilitating weight loss in a subject, comprising the step of administering to the subject the selective androgen receptor modulator (SARM)/s as described herein and/or an analog, derivative, isomer, metabolite, pharmaceutically acceptable salt, pharmaceutical product, hydrate, N-oxide, prodrug, polymorph, crystal, or any combination thereof, in an amount effective to promote, increase or facilitate weight loss in the subject.

In another embodiment, this invention relates to a method of decreasing, suppressing, inhibiting or reducing appetite of a subject, comprising the step of administering to the subject a selective androgen receptor modulator (SARM)/s as described herein and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject.

In another embodiment, this invention relates to a method of altering the body composition of a subject, comprising the step of administering to the subject a selective androgen receptor modulator (SARM) as described herein and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof.

In another embodiment, this invention relates to a method of altering lean body mass or fat free body mass of a subject, comprising the step of administering to the subject a selective androgen receptor modulator (SARM)/s as described herein and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat free body mass of the subject.

In another embodiment, this invention relates to a method of converting fat to lean muscle in a subject, comprising the step of administering to the subject a selective androgen receptor modulator (SARM)/s as described herein and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject.

In another embodiment, this invention relates to a method of treating an obesity-associated metabolic disorder in a subject, comprising the step of administering to the subject a selective androgen receptor modulator (SARM)/s as described herein and/or its analog, derivative, isomer, metabolite, pharmaceutically acceptable salt, pharmaceutical product, hydrate, N-oxide, prodrug, polymorph, crystal, or any combination thereof, in an amount effective to treat the obesity-associated metabolic disorder in the subject.

In another embodiment, this invention relates to a method of preventing, suppressing, inhibiting or reducing an obesity-associated metabolic disorder in a subject, comprising the step of administering to the subject a selective androgen receptor modulator (SARM)/s as described herein and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the obesity-associated metabolic disorder in the subject.

In one embodiment, the obesity-associated metabolic disorder is hypertension. In another embodiment, the disorder is osteoarthritis. In another embodiment, the disorder is Type II diabetes mellitus. In another embodiment, the disorder is increased blood pressure. In another embodiment, the disorder is stroke. In another embodiment, the disorder is heart disease.

In another embodiment, this invention relates to a method of decreasing, suppressing, inhibiting or reducing adipogenesis in a subject, comprising the step of administering to the subject a selective androgen receptor modulator (SARM)/s as described herein and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce adipogenesis in the subject.

In one embodiment, the SARM that is useful in a) treating, preventing, suppressing, inhibiting, or reducing obesity; b) promoting, increasing or facilitating weight loss; c) decreasing, suppressing, inhibiting or reducing appetite; d) altering the body composition; e) altering lean body mass or fat free body mass; f) converting fat to lean muscle; g) treating, preventing, suppressing, inhibiting, or reducing an obesity-associated metabolic disorder, for example hypertension, osteoarthritis, Type II diabetes mellitus, increased blood pressure, stroke, or heart disease; h) decreasing, suppressing, inhibiting or reducing adipogenesis; i) altering stem cell differentiation; and/or j) altering the level of leptin, is a compound represented by the structure of XX.

In one embodiment, the SARMs of this invention find utility in treating or halting the progression of, or treating symptoms of diabetes. In one embodiment, the administration of the SARM/s as described herein to a subject at risk of diabetes, or in other embodiments, other metabolic disorders, may alter progression of the disease, or in another embodiment, prevent disease, or in another embodiment, reduce the severity, or in another embodiments, reduce symptoms associated with the disease. In one embodiment, the treatment is initiated upon first indication of a risk factor, or in another embodiment, upon evidence of early stages of disease, as will be appreciated by one skilled in the art. For example, and in one embodiment, treatment of a subject may be initiated with the subject's presentation of hyperinsulinemia, or in another embodiment, gestational diabetes, or in another embodiment, hyperglycemia, or in another embodiment, impaired glucose tolerance, etc., as will be appreciated by one skilled in the art.

In another embodiment, the SARMs as described herein are useful in treating co-morbidities related to diabetes. These conditions include: hypertension, cerebrovascular disease, atherosclerotic coronary artery disease, macular degeneration, diabetic retinopathy (eye disease) and blindness, cataracts—systemic inflammation (characterized by elevation of inflammatory markers such as erythrocyte sedimentation rate or C-reactive protein), birth defects, pregnancy related diabetes, pre-ecclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (non-alcoholic steatohepatitis, or NASH), and diabetes-related skin diseases such as Necrobiosis Lipoidica Diabeticorum (NLD), Blisters of diabetes (Bullosis Diabeticorum), Eruptive Xanthomatosis, Digital Sclerosis, Disseminated Granuloma Annulare, and Acanthosis Nigricans.

In one embodiment this invention provides a method for a) treating, preventing, suppressing inhibiting atherosclerosis b) treating, preventing, suppressing inhibiting liver damage due to fat deposits comprising the step of administering to the subject a selective androgen receptor modulator (SARM)/s as described herein and/or its analog, derivative, isomer, metabolite, pharmaceutically acceptable salt, pharmaceutical product, hydrate, N-oxide, prodrug, polymorph, crystal, or any combination thereof, or a composition comprising the same, in an amount effective to treat, prevent or inhibit atherosclerosis and liver damage due to fat deposit.

In one embodiment, the SARM/s as described herein is useful in a) treating, preventing, suppressing, inhibiting, or reducing atherosclerosis; b) treating, preventing, suppressing inhibiting liver damage due to fat deposits.

In one embodiment atherosclerosis refers to a slow, complex disease that may begin with damage to the innermost layer of the artery. In another embodiment the causes of damage to the arterial wall may include a) elevated levels of cholesterol and in the blood; b) high blood pressure; c) tobacco smoke d) diabetes. In another embodiment, the condition is treatable in a smoker, despite the fact that tobacco smoke may greatly worsen atherosclerosis and speed its growth in the coronary arteries, the aorta and arteries in the legs. Similarly, in another embodiment, the methods of this invention may be useful in treating subjects with a family history of premature cardiovascular disease who have an increased risk of atherosclerosis.

In one embodiment, liver damage due to fat deposits refer to the build-up of fat in the liver cells forming a Fatty Liver which may be associated with or may lead to inflammation of the liver. This can cause scarring and hardening of the liver. When scarring becomes extensive, it is called cirrhosis.

In another embodiment the fat accumulates in the liver as obesity. In another embodiment fatty liver is also associated with diabetes mellitus, high blood triglycerides, and the heavy use of alcohol. In another embodiment fatty Liver may occur with certain illnesses such as tuberculosis and malnutrition, intestinal bypass surgery for obesity, excess vitamin A in the body, or the use of certain drugs such as valproic acid (trade names: Depakene/Depakote) and corticosteroids (cortisone, prednisone). Sometimes fatty liver occurs as a complication of pregnancy. In one embodiment, the SARM/s as described herein may be used to treat any of these conditions, and represents another embodiment of this invention. In one embodiment, use of the SARM of Compound XX will not result in toxic effects in the liver, even with prolonged use.

In another embodiment, the SARM of Compound XX will be useful in treating wasting conditions which, in some embodiments, result in bone degradation or fracture. In one embodiment, the SARM is useful in treating bone diseases or disorders, irrespective of the presence of wasting in the subject.

In one embodiment, this invention provides for the use of a Compound XX, or its prodrug, analog, isomer, metabolite, derivative, pharmaceutically acceptable salt, pharmaceutical product, polymorph, crystal, impurity, N-oxide, hydrate or any combination thereof, for 1) treating a bone related disorder; 2) preventing a bone related disorder; 3) suppressing a bone related disorder; 4) inhibiting a bone related disorder; 5) increasing a strength of a bone of a subject; 5) increasing a bone mass in a subject; 6) use for osteoclastogenesis inhibition.

In one embodiment, the bone related disorder is a genetic disorder, or in another embodiment, is induced as a result of a treatment regimen for a given disease. For example, and in one embodiment, the SARMs are useful in treating a bone-related disorder that arises as a result of androgen-deprivation therapy, given in response to prostate carcinogenesis in a subject.

In one embodiment, the present invention provides a use of the SARM compound for preventing a bone-related disorder in a subject. In another embodiment, the present invention provides a use of the SARM compound for suppressing a bone-related disorder in a subject. In another embodiment, the present invention provides a use of the SARM compound for inhibiting a bone-related disorder in a subject or its prodrug, analog, isomer, metabolite, derivative, pharmaceutically acceptable salt, pharmaceutical product, polymorph, crystal, impurity, N-oxide, hydrate or any combination thereof.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty. In another embodiment, the bone-related disorder is a loss of BMD. In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In another embodiment, the primary osteoporosis is Type I primary osteoporosis. In another embodiment, the primary osteoporosis is Type II primary osteoporosis. Each type of osteoporosis represents a separate embodiment of the present invention.

Osteoporosis and osteopenia are, in another embodiment, systemic skeletal diseases characterized by low bone mass and microarchitectural deterioration of bone tissue. "Microarchitectural deterioration" refers, in one embodiment, to thinning of the trabeculae (defined below) and the loss of inter-trabecular connections in bone. In another embodiment, "osteoporosis" is defined as having a BMD 2.5 standard deviations (SD) or more below the young adult mean. In another embodiment, "osteoporosis" is defined as having a BMC 2.5 SD or more below the young adult mean. In another embodiment, "osteoporosis" is defined as having a BMD 2.0 SD or more below the young adult mean. In another embodiment, "osteoporosis" is defined as having a BMC 2.0 SD or more below the young adult mean. In another embodiment, "osteoporosis" is defined as having a BMD 3.0 SD or more below the young adult mean. In another embodiment, "osteoporosis" is defined as having a BMC 3.0 SD or more below the young adult mean. Each definition of osteoporosis or osteopenia represents a separate embodiment of the present invention.

In another embodiment, "osteoporosis" is defined as having a BMD 2.5 SD below the young adult mean. In another embodiment, "osteoporosis" is defined as having a BMC 2.5 SD below the young adult mean. In another embodiment, "osteoporosis" is defined as having a BMD 2.0 SD below the young adult mean. In another embodiment, "osteoporosis" is defined as having a BMC 2.0 SD below the young adult mean. In another embodiment, "osteoporosis" is defined as having a BMD 3.0 SD below the young adult mean. In another embodiment, "osteoporosis" is defined as having a BMC 3.0 SD below the young adult mean. Each definition of osteoporosis represents a separate embodiment of the present invention.

Methods for assessing osteoporosis and osteopenia are well known in the art. For example, in one embodiment, a patient's BMD, measured by densitometry and expressed in g/cm2, is compared with a "normal value," which is the mean BMD of sex-matched young adults at their peak bone mass, yielding a "T score." In another embodiment, Z-score, the amount of bone loss in a patient is compared with the expected loss for individuals of the same age and sex. In another embodiment, "osteoporosis" is defined as having a T score 2.5 SD or more below the young adult mean. In another embodiment, "osteoporosis" is defined as having a Z score 2.5 SD or more below the young adult mean. In another embodiment, "osteoporosis" is defined as having a T score 2.0 SD or more below the young adult mean. In another embodiment, "osteoporosis" is defined as having a Z score 2.0 SD or more below the young adult mean. In another embodiment, "osteoporosis" is defined as having a T score 3.0 SD or more below the young adult mean. In another embodiment, "osteoporosis" is defined as having a Z score 3.0 SD or more below the young adult mean.

In another embodiment, "osteoporosis" is defined as having a T score 2.5 SD below the young adult mean. In another embodiment, "osteoporosis" is defined as having a Z score 2.5 SD below the young adult mean. In another embodiment, "osteoporosis" is defined as having a T score 2.0 SD below the young adult mean. In another embodiment, "osteoporosis" is defined as having a Z score 2.0 SD below the young adult mean. In another embodiment, "osteoporosis" is defined as having a T score 3.0 SD below the young adult mean. In another embodiment, "osteoporosis" is defined as having a Z score 3.0 SD below the young adult mean. Each definition of osteoporosis represents a separate embodiment of the present invention.

The term "BMD" is, in one embodiment, a measured calculation of the true mass of bone. The absolute amount of bone as measured by BMD generally correlates with bone strength and its ability to bear weight. By measuring BMD, it is possible to predict fracture risk in the same manner that measuring blood pressure can help predict the risk of stroke.

BMD, in one embodiment, can be measured by known BMD mapping techniques. In one embodiment, bone density of the hip, spine, wrist, or calcaneus may be measured by a variety of techniques. The preferred method of BMD measurement is dual-energy x-ray densitometry (DEXA). BMD of the hip, antero-posterior (AP) spine, lateral spine, and wrist can be measured using this technology. Measurement at any site predicts overall risk of fracture, but information from a specific site is the best predictor of fracture at that site. Quantitative computerized tomography (QCT) is also used to measure BMD of the spine. See for example, "Nuclear Medicine: Quantitative Procedures" by Wahner H W, et al, published by Toronto Little, Brown & Co., 1983, pages 107-132; "Assessment of Bone Mineral Part 1," J Nucl Medicine, pp 1134-1141 (1984); and "Bone Mineral Density of The Radius" J Nucl Medicine 26: 13-39 (1985). Each method of measuring BMD represents a separate embodiment of the present invention.

"Osteopenia" refers, in one embodiment, to having a BMD or BMC between 1 and 2.5 SD below the young adult mean. In another embodiment, "osteopenia" refers to decreased calcification or density of bone. This term encompasses, in one embodiment, all skeletal systems in which such a condition is noted. Each definition or means of diagnosis of the disorders disclosed in the present invention represents a separate embodiment of the present invention.

In one embodiment, the term "bone fracture" refers to a breaking of bones, and encompasses both vertebral and non-vertebral bone fractures. The term "bone frailty" refers, in one embodiment, to a weakened state of the bones that predisposes them to fractures.

In one embodiment, the bone-related disorder is treated with a SARM compound of this invention, or a combination thereof. In another embodiment, other bone-stimulating compounds can be provided to a subject, prior to, concurrent with or following administration of a SARM or SARMs of this invention. In one embodiment, such a bone stimulating compound may comprise natural or synthetic materials.

In one embodiment, the bone stimulating compound may comprise a bone morphogenetic protein (BMP), a growth factor, such as epidermal growth factor (EGF), a fibroblast growth factor (FGF), a transforming growth factor (TGF-α or TGF-β), an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, frizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the art.

In another embodiment, the compositions for use in treating a bone disorder of this invention may comprise a SARM or SARMs as described herein, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast.

In another embodiment, nucleic acids which encode bone-stimulating compounds may be administered to the subject, which is to be considered as part of this invention.

In one embodiment, the osteoporosis, osteopenia, increased bone resorption, bone fracture, bone frailty, loss of BMD, and other diseases or disorders of the present invention are caused by a hormonal disorder, disruption or imbalance. In another embodiment, these conditions occur independently of a hormonal disorder, disruption or imbalance. Each possibility represents a separate embodiment of the present invention.

In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject.

Each possibility represents a separate embodiment of the present invention.

In one embodiment, the invention provides a use of the SARM compounds or its prodrug, analog, isomer, metabolite, derivative, pharmaceutically acceptable salt, pharmaceutical product, polymorph, crystal, impurity, N-oxide, hydrate or any combination thereof for increasing a strength of a bone of a subject.

In another embodiment, the subject has an osteoporosis. In another embodiment the osteoporosis is hormonally induced.

In one embodiment, the invention provides a use of the SARM compounds for increasing a bone mass of a subject.

In another embodiment, the subject has osteoporosis. In another embodiment the osteoporosis is hormonally induced. In another embodiment the subject has sarcopenia or cachexia. In another embodiment the methods of this invention provide for increasing a bone mass in the subject, which is a cortical bone mass. In another embodiment the bone mass is trabecular bone mass. In another embodiment the bone mass is a cancellous bone mass.

In another embodiment, the SARM compound stimulates or enhances osteoblastogenesis. In another embodiment, the said SARM compound inhibits osteoclast prolification.

In one embodiment, the invention provides for bone formation via osteoblast stimulation or enhanced proliferation. In one embodiment, the term "osteoblast" refers to cell which participates in bone-formation. In one embodiment, osteoblast involvement in bone formation may form the tissue and deposit minerals therein, giving bone its strength. In another embodiment, the invention provides for bone formation via suppression of osteoclast induction, or in another embodiment, activity. In one embodiment, the term "osteoclast" refers to a cell which participates in bone remodeling, and in particular in bone resorption.

In one embodiment, bone diseases or disorders are treated by the methods of this invention via stimulation of bone formation. In another embodiment, the treatments of this invention provide for maintenance of bone mass. Bone mass is maintained by a balance between the activity of osteoblasts that form bone and osteoclasts that break it down. In one embodiment, the compounds and methods of this invention provide a means whereby such a balance is maintained.

In one embodiment, the treatment methods as described herein are selective in that they do not promote androgenic effects. In one embodiment, this is manifest in an absence of change of PSA levels in males. In another embodiment, this is manifest in an absence of effect on sebaceous glands. In another embodiment, this is manifest in an absence of effects on hair loss.

The following examples are presented in order to more fully illustrate certain embodiments of the invention. They should in no way be construed, however, as limiting the broad scope of the invention.

EXPERIMENTAL DETAILS SECTION

Example 1

The effect of Compound XX, a selective androgen receptor modulator represented by the formula:

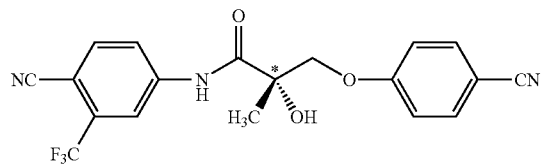

XX was evaluated in a human clinical trial.

Healthy male volunteers, 18-45 years of age, and elderly males with truncal obesity, who averaged 68 years of age, were enrolled in the trial and assigned to groups, including controls, given placebo, or those treated with the compound, given multiple-ascending doses of the Compound, respectively.

Safety and pharmacodynamic measurements were taken at the beginning of the study and after 14 days of daily oral dosing. These measurements included routine blood chemistry and hematology, sex hormones and gonadotropins, serum prostate specific antigen, metabolic markers of bone and muscle, cutaneous sebum analysis and DEXA scanning for body composition.

Subjects administered Compound XX demonstrated clinical laboratory values and hormonal effects consistent with anabolic activity. Comparisons of DEXA assessments from the beginning of the study to DEXA assessments after 14 days showed positive changes in body composition, with lean body mass and fat mass in study patients moving in a direction consistent with anabolic activity.

Based on other tests, Compound XX did not appear to have unwanted side effects on the prostate or the skin.

What is claimed is:

1. A method of treating a human subject suffering from a wasting disorder, or suppressing or reducing the incidence of a wasting disorder in a subject, comprising the step of administering to said subject a selective androgen receptor modulator (SARM) compound of formula XX:

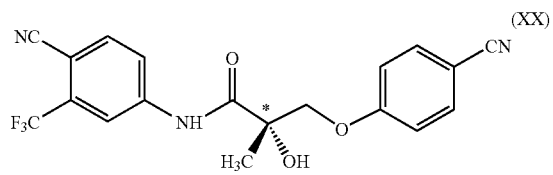

(XX)

and/or its isomer, pharmaceutically acceptable salt or any combination thereof.

2. The method of claim 1, wherein said wasting disorder is due to a pathology, illness, disease or condition.

3. The method of claim 2, wherein said pathology, illness, disease or condition is neurological, infectious, chronic or genetic.

4. The method of claim 2, wherein said pathology, illness, disease or condition is cachexia, malnutrition, leprosy, tuberculosis, diabetes, renal disease, chronic obstructive pulmonary disease, cancer, end stage renal failure, emphysema, osteomalacia, HIV infection, AIDS, andropause, frailty or cardiomyopathy.

5. The method according to claim 1, wherein said wasting disorder is age-associated or is due to chronic lower back pain, burns, central nervous system injury or damage, peripheral nerve injury or damage, spinal cord injury or damage, chemical injury or damage, or alcoholism.

6. The method of claim 1, wherein said wasting disorder is a muscle wasting disorder.

7. The method of claim 6, wherein said muscle wasting disorder is due to a muscular dystrophy, a muscular atrophy, an X-linked spinal-bulbar muscular atrophy, or sarcopenia.

8. The method according to claim 6, wherein said muscle wasting disorder is a disuse deconditioning-associated muscle wasting disorder.

9. The method according to claim 6, wherein said muscle wasting disorder is a chronic muscle wasting disorder.

10. The method according to claim 1, wherein said administering comprises administering a composition comprising said SARM, and/or its isomer, pharmaceutically acceptable salt, or any combination thereof, and a pharmaceutically acceptable carrier.

11. The method according to claim 10, wherein said administering comprises intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

12. The method according to claim 10, wherein said pharmaceutical composition is a pellet, a tablet, a capsule, a solution, a suspension, an emulsion, an elixir, a gel, a cream, a suppository or a parenteral formulation.

* * * * *